US010813796B2

(12) United States Patent
Umemoto

(10) Patent No.: US 10,813,796 B2
(45) Date of Patent: Oct. 27, 2020

(54) UNDERPANTS-TYPE DISPOSABLE DIAPER WITH DYNAMIC FIT

(71) Applicant: DAIO PAPER CORPORATION, Ehime (JP)

(72) Inventor: Kaori Umemoto, Tochigi (JP)

(73) Assignee: DAIO PAPER CORPORATION, Ehime (JP)

( * ) Notice: Subject to any disclaimer, the term of this patent is extended or adjusted under 35 U.S.C. 154(b) by 857 days.

(21) Appl. No.: 15/512,373

(22) PCT Filed: Sep. 28, 2015

(86) PCT No.: PCT/JP2015/077339
§ 371 (c)(1),
(2) Date: Mar. 17, 2017

(87) PCT Pub. No.: WO2016/052414
PCT Pub. Date: Apr. 7, 2016

(65) Prior Publication Data
US 2017/0273833 A1    Sep. 28, 2017

(30) Foreign Application Priority Data

Sep. 29, 2014   (JP) ................................ 2014-198646

(51) Int. Cl.
*A61F 13/15*   (2006.01)
*A61F 13/20*   (2006.01)
(Continued)

(52) U.S. Cl.
CPC ...... *A61F 13/49406* (2013.01); *A61F 13/496* (2013.01); *A61F 13/515* (2013.01);
(Continued)

(58) Field of Classification Search
CPC ............ A61F 13/49406; A61F 13/5655; A61F 2013/4575; A61F 13/49017; A61F 13/496;
(Continued)

(56) References Cited

U.S. PATENT DOCUMENTS 4,895,568 A * 1/1990 Enloe .................. A61F 13/4758
                                                    604/385.27
5,554,142 A * 9/1996 Dreier .................. A61F 13/495
                                                    604/385.23
(Continued)

FOREIGN PATENT DOCUMENTS

EP       2835122      *  2/2015 ............ A61F 13/49
EP       3199134 A1    8/2017
(Continued)

*Primary Examiner* — Michele M Kidwell
(74) *Attorney, Agent, or Firm* — Muncy, Geissler, Olds & Lowe, P.C.

(57) ABSTRACT

The present invention is intended to improve the dynamic fit of a crotch portion. The foregoing issue is solved in such a manner that a vertical stretchable part vertically extending and contracting in length is provided in a vertical intermediate portion of an absorber in a front body, an outer body of the front body has a portion overlapping at least the vertical stretchable part, width-direction both side sections of the portion, and a waist opening-side area of the portion and the sections, lifting elastic members having a contraction force of lifting a portion of the vertical stretchable part on a rear side of a front end toward width-direction both sides and an obliquely upward side at least when the diaper is worn are provided in the outer body of the front body on closer to lateral sides than to a width-direction intermediate portion of the absorber, and the vertical stretchable part vertically extends and contracts in length by elastic extension and contraction of the lifting elastic member.

7 Claims, 12 Drawing Sheets

(51) Int. Cl.
*A61F 13/494* (2006.01)
*A61F 13/496* (2006.01)
*A61F 13/53* (2006.01)
*A61F 13/532* (2006.01)
*A61F 13/515* (2006.01)
*A61F 13/56* (2006.01)
*A61F 13/45* (2006.01)
*A61F 13/49* (2006.01)

(52) U.S. Cl.
CPC ............ *A61F 13/53* (2013.01); *A61F 13/532* (2013.01); *A61F 13/5655* (2013.01); *A61F 13/49011* (2013.01); *A61F 2013/4575* (2013.01); *A61F 2013/530481* (2013.01)

(58) Field of Classification Search
CPC ...... A61F 13/53; A61F 13/532; A61F 13/515; A61F 13/49011
See application file for complete search history.

(56) References Cited

U.S. PATENT DOCUMENTS

| | | | | |
|---|---|---|---|---|
| 5,735,839 | A * | 4/1998 | Kawaguchi | A61F 13/49009 604/385.29 |
| 5,745,922 | A * | 5/1998 | Rajala | A61F 13/15593 2/243.1 |
| 6,508,798 | B1 * | 1/2003 | Widlund | A61F 13/495 604/385.27 |
| 6,648,868 | B2 * | 11/2003 | Sayama | A61F 13/49019 604/385.22 |
| 7,594,907 | B2 * | 9/2009 | Otsubo | A61F 13/49017 604/385.03 |
| 8,197,457 | B2 * | 6/2012 | Suzuki | A61F 13/495 604/385.24 |
| 9,050,218 | B2 * | 6/2015 | Martynus | A61F 13/49406 |
| 9,050,219 | B2 * | 6/2015 | Martynus | A61F 13/49017 |
| 9,119,750 | B2 * | 9/2015 | Suzuki | A61F 13/4946 |
| 10,406,041 | B2 * | 9/2019 | Mori | A61F 13/51476 |
| 2002/0013567 | A1 * | 1/2002 | Mishima | A61F 13/4946 604/385.101 |
| 2002/0068919 | A1 * | 6/2002 | Shinohara | A61F 13/49017 604/385.27 |
| 2002/0143313 | A1 * | 10/2002 | Tsuji | A61F 13/49017 604/385.03 |
| 2002/0147438 | A1 * | 10/2002 | Tanaka | A61F 13/49019 604/392 |
| 2004/0133180 | A1 | 7/2004 | Mori et al. | |
| 2005/0203477 | A1 * | 9/2005 | Mishima | A61F 13/495 604/385.28 |
| 2006/0009746 | A1 * | 1/2006 | Nakajima | A61F 13/4915 604/385.19 |
| 2006/0025746 | A1 | 2/2006 | Sasaki et al. | |
| 2006/0122570 | A1 | 6/2006 | Kasai | |
| 2006/0135931 | A1 * | 6/2006 | Suzuki | A61F 13/495 604/385.19 |
| 2007/0156110 | A1 * | 7/2007 | Thyfault | A61F 13/494 604/385.101 |
| 2010/0331805 | A1 * | 12/2010 | Nakajima | A61F 13/495 604/385.28 |
| 2011/0015606 | A1 | 1/2011 | Nakajima et al. | |
| 2014/0221955 | A1 * | 8/2014 | Brown | A61F 13/495 604/385.28 |
| 2015/0073373 | A1 * | 3/2015 | Mukai | A61F 13/49001 604/385.29 |

FOREIGN PATENT DOCUMENTS

| | | |
|---|---|---|
| JP | 4-28363 A | 1/1992 |
| JP | 11-332913 A | 12/1999 |
| JP | 2002-35029 A | 2/2002 |
| JP | 2002-178428 A | 6/2002 |
| JP | 2002-273808 A | 9/2002 |
| JP | 2004-141270 A | 5/2004 |
| JP | 2004-236832 A | 8/2004 |
| JP | 2006-043067 A | 2/2006 |
| JP | 2006-061680 A | 3/2006 |
| JP | 2009-082483 A | 4/2009 |
| JP | 2011-177309 A | 9/2011 |
| JP | 2014-150899 A | 8/2014 |

* cited by examiner

UNDERPANTS-TYPE DISPOSABLE DIAPER WITH DYNAMIC FIT

TECHNICAL FIELD

The present invention relates to an underpants-type disposable diaper improved in the dynamic fit of a crotch portion.

BACKGROUND ART

An underpants-type disposable diaper includes an outer body forming individually or integrally a front body and a back body, and an inner body that has an absorber and is attached to the inner surface of the outer body from the front body to the back body. In general, the outer body of the front body and the outer body of the back body are joined together at the both sides to form side seal portions, thereby forming a waist opening and a pair of right and left leg openings. The underpants-type disposable diaper also generally has elastic members such as rubber threads in the leg portions and the waist part to improve the fit (for example, see Patent Document 1).

However, the absorber existence region in the crotch portion is not suited to the improvement of the fit by the elastic members. Specifically, when an attempt is made to elastically extend and contract the absorber existence region by the elastic members, no sufficient amount of stretch can be obtained due to the rigidity of the absorber. Even if a sufficient amount of stretch can be obtained, irregular asperities would occur on the absorber to cause a stiff feeling and liquid leakage. Accordingly, at present, no elastic members are generally provided in the absorber existence region where possible.

Therefore, the fit of the absorber existence region in the crotch portion is conventionally insufficient. Various patent documents such as Patent Documents 1 and 2 have proposed techniques for improvement of a static fit in particular. However, the crotch portion undergoes large dynamic changes due to expansion and contraction and back-and-forth movement caused by the wearer's motion or changes in the volume of the absorber between before and after absorption. The improvement of a dynamic fit against such changes is desired.

CITATION LIST

Patent Documents

Patent Document 1: JP-A No. 2006-43067
Patent Document 2: JP-A No. 2011-177309

SUMMARY OF INVENTION

Technical Problem

A major object of the present invention is to improve the dynamic fit of the crotch portion.

Solution to Problem

The present invention having solved the foregoing problem is as follows:
<The invention of claim 1>
An underpants-type disposable diaper comprising
an outer body forming individually or integrally a front body and a back body; and
an absorber provided on the inner side of the outer body ranging from the front body to the back body,
the outer body of the front body and the outer body of the back body being joined together at both side edges to form side seal portions, thereby forming a waist opening and a pair of right and left leg openings, wherein
a vertical stretchable part vertically extending and contracting in length is provided in a vertical intermediate portion of the absorber in the front body,
the outer body of the front body has a portion overlapping at least the vertical stretchable part, width-direction both side sections of the portion, and a waist opening-side area of the portion and the sections,
lifting elastic members having a contraction force of lifting a portion of the vertical stretchable part on a rear side of a front end portion toward width-direction both sides and obliquely upward sides at least when the diaper is worn are provided in the outer body of the front body on closer to lateral sides than to a width-direction intermediate portion of the absorber, and
the vertical stretchable part vertically extends and contracts in length by elastic extension and contraction of the lifting elastic member.

Operation and Effect

According to the present invention, the vertical stretchable part is vertically extended and contracted in length to maintain the fit by the elastic extension and contraction of the lifting elastic members in accordance with dynamic changes such as the wearer's motion and changes in the volume of the absorber between before and after absorption, thereby providing a more excellent dynamic fit. In addition, the lifting elastic members are provided on closer to lateral sides than to the width-direction intermediate portion of the absorber as are conventionally done, and the absorber does not contract largely.
<The invention of claim 2>
The underpants-type disposable diaper according to claim 1, wherein leg opening elastic members composed of elongated elastic members along a width direction are provided in the outer body of the front body in vertical ranges corresponding to the leg openings on closer to lateral sides than to the width-direction intermediate portion of the absorber, and
when the diaper is worn, the leg opening elastic members are oriented obliquely upward in a lateral direction and at least some of the leg opening elastic members constitute the lifting elastic members.

Operation and Effect

In the underpants-type disposable diaper, the leg opening elastic members composed of elongated elastic members along the width direction are provided in the vertical ranges corresponding to the leg openings. When the diaper is opened, the leg opening elastic members are aligned along the width direction. However, when the diaper is worn, the leg opening elastic members are oriented obliquely upward in the lateral direction and have a contraction force in that direction because the width-direction both sides of the diaper are lifted relatively upward in the worn state. The invention of claim 2 utilizes these leg opening elastic members as the lifting elastic members, which provides the advantage that there is no need to provide any dedicated elastic members.

<The invention of claim 3>

The underpants-type disposable diaper according to claim 1 or 2, wherein the outer body of the front body includes basic elastic members, which are different from the lifting elastic members below the waist portion to improve a fit, and the contraction force of the lifting elastic members is smaller than the contraction force of the basic elastic members at the same elongation percentage.

Operation and Effect

Making a difference in contraction force as described above allows the outer body to fit more firmly by the basic elastic members and allows the vertical stretchable part to move more easily with the firmed fit as a support.

<The invention of claim 4>

The underpants-type disposable diaper according to any one of claims 1 to 3, wherein the outer body of the front body includes side portion elastic members, which are different from the lifting elastic members, on closer to lateral sides than to the width-direction intermediate portion of the absorber to improve a fit, and end portions of the side portion elastic members on a width-direction central side are laterally more separated from side edges of the absorber than end portions of the lifting elastic members on a width-direction central side.

Operation and Effect

Providing the side portion elastic members as described above enables to ensure the basic fit of the absorber on the width-direction both sides, and to make the lifting action of the lifting elastic members less affected by the contraction force of the side portion elastic members. This allows favorably the lifting action of the lifting elastic members to exert on the vertical stretchable part in a more direct manner.

<The invention of claim 5>

The underpants-type disposable diaper according to any one of claims 1 to 4, wherein the outer body of the front body includes curved elastic members composed of elongated elastic members arranged from the side seal portions to a crotch portion along the leg openings, and at least some of the curved elastic members constitute the lifting elastic members.

Operation and Effect

In the underpants-type disposable diaper, the curved elastic members are provided from the side seal portions to the crotch portion along the leg openings, and the curved elastic members are oriented obliquely upward in the lateral direction and act the contraction force in that direction. The invention of claim 5 utilizes these curved elastic members as the lifting elastic members, which provides the advantage that there is no need to provide any dedicated elastic members.

<The invention of claim 6>

The underpants-type disposable diaper according to any one of claims 1 to 5, wherein the vertical stretchable part is a slit or a low-basis weight part continuous on the entire absorber in the width direction, and a plurality of the vertical stretchable parts is provided at vertical intervals.

Operation and Effect

The vertical stretchable part can be formed from a slit or a low-basis weight part continuous on the entire absorber in the width direction. However, when the vertical stretchable part is longer in the front-back direction, the part will decrease in diffusivity in the front-back direction. Accordingly, by spacing a plurality of the vertical stretchable parts in the front-back direction as described above, even though the total stretching length of the vertical stretchable parts is the same as the length of the long vertical stretchable part, the dimension in the front-back direction of one vertical stretchable part will become shorter. This makes it possible to suppress reduction in the diffusivity in the front-back direction.

<The invention of claim 7>

The underpants-type disposable diaper according to any one of claims 1 to 6, wherein the vertical stretchable part has a front edge curved backward or a back edge curved forward, or both.

Operation and Effect

By shaping the front and back edges of the vertical stretchable part in this manner, the part of the absorber on the front side of the vertical stretchable part is likely to swing side to side with respect to the part of the absorber on the rear side of the vertical stretchable part, thereby providing a more excellent dynamic fit.

Advantageous Effects of Invention

As described above, according to the present invention, it is possible to provide the advantage of improvement in the dynamic fit of the crotch portion and others.

DESCRIPTION OF EMBODIMENT

Figure 1:
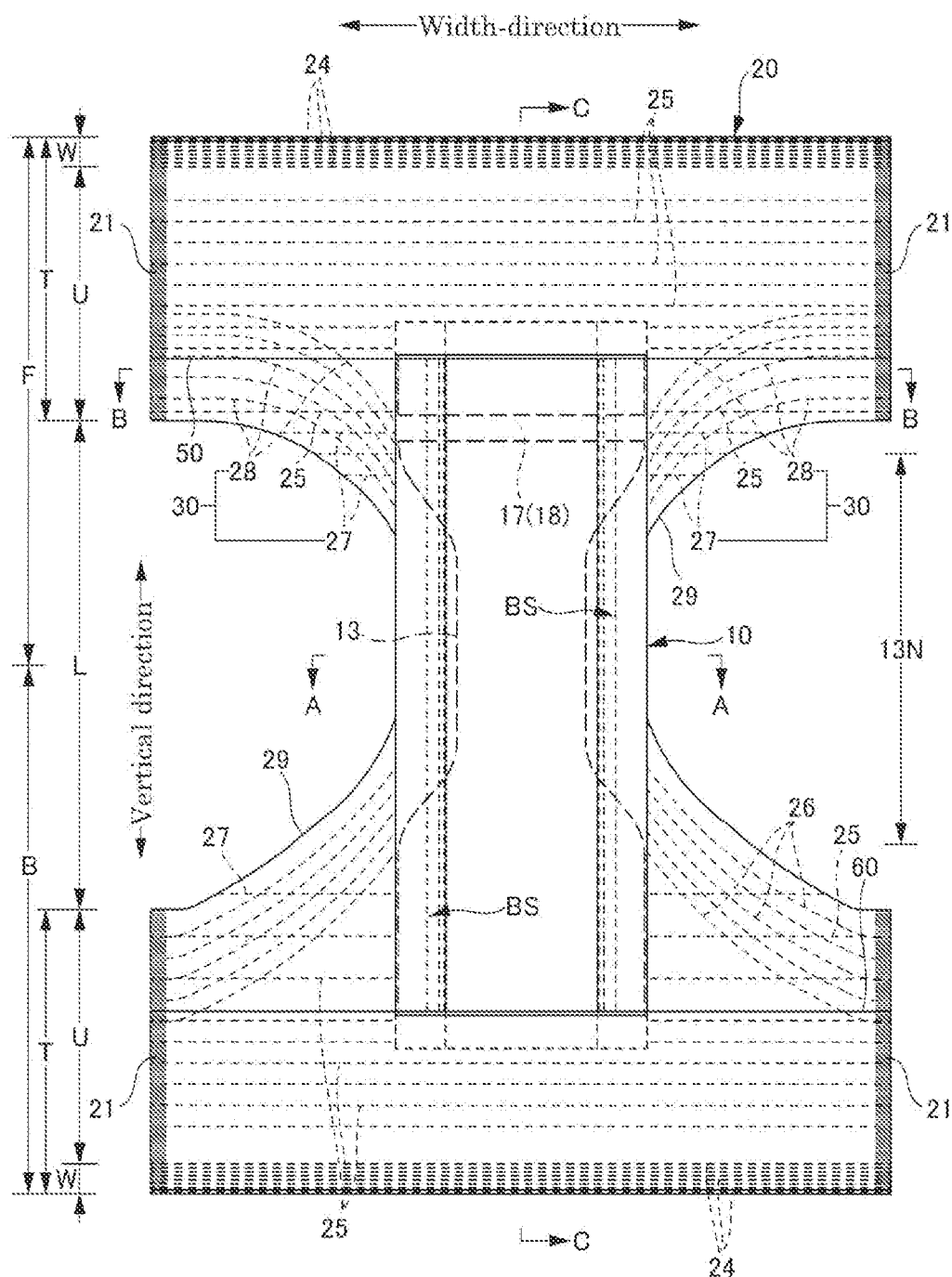
FIG. 1 is a plane view (inner surface side) of an underpants-type disposable diaper in an open state.
Figure 2:
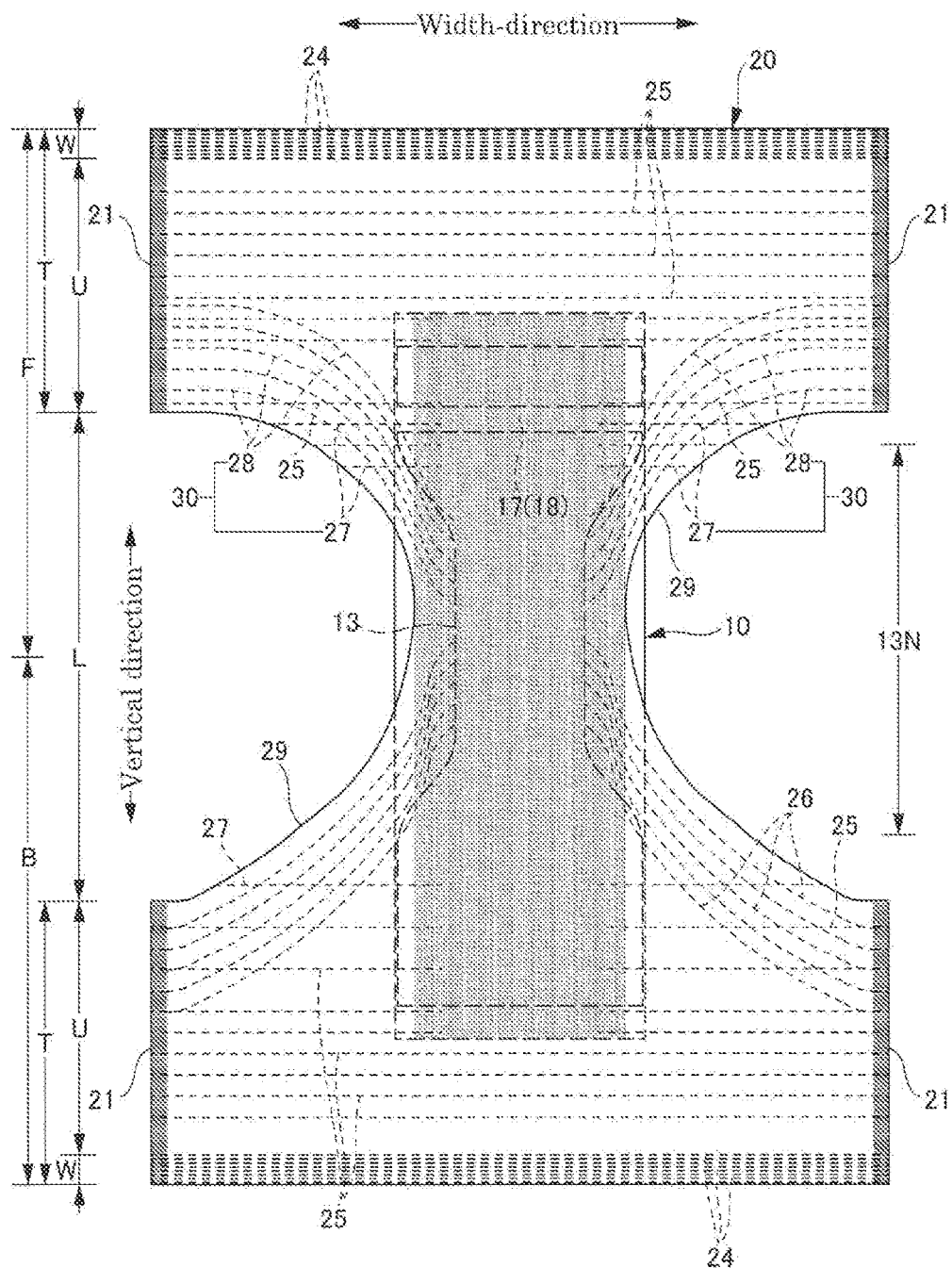
FIG. 2 is a plane view (outer surface side) of the underpants-type disposable diaper in the open state.
Figure 3:
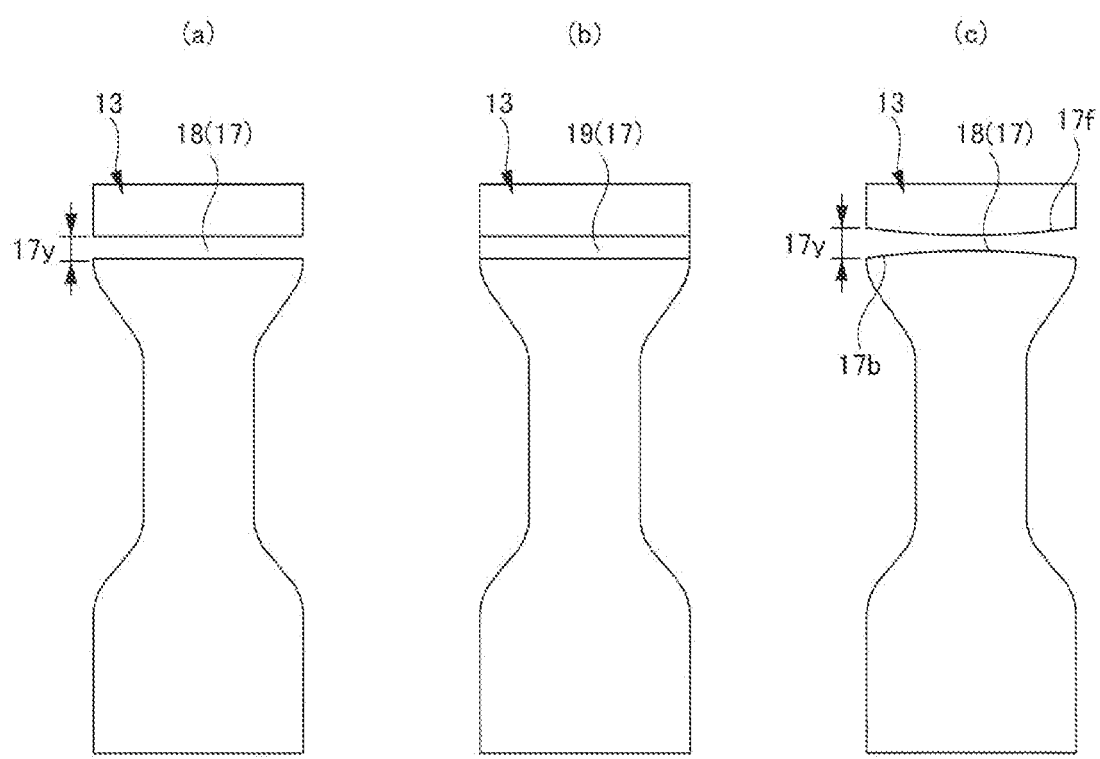
FIGS. 3(a) to 3(c) are plane views of an absorber.

One embodiment of the present invention will be described in detail with reference to the accompanied drawings. The "extension ratio" herein takes on a value relative to the natural length as 100%. The dot patterns in the drawings represent a joining means such as a hot-melt adhesive.

FIGS. 1 to 8 illustrate an example of underpants-type disposable diaper. The underpants-type disposable diaper (hereinafter, also simply called diaper) has an outer body 20 constituting integrally a front body F and a back body B and an inner body 10 fixed to the inner surface of the outer body 20 ranging from the front body F to the back body B. The inner body 10 is formed by interposing an absorber 13 between a liquid pervious face sheet 11 and a liquid impervious back sheet 12. In manufacturing, for example, the back surface of the inner body 10 is joined to the inner surface (upper surface) of the outer body 20 by a joining means such as a hot-melt adhesive (as illustrated in the dot-patterned part of FIG. 2), then the inner body 10 and the outer body 20 are folded in the center in the front-back (vertical) direction as a boundary between the front body F and the back body B, and then the both side parts are joined together by heat welding, a hot-melt adhesive, or the like to form side seal portions 21, thereby obtaining the underpants-type disposable diaper having a waist opening and a pair of right and left leg openings.

(Structure Example of the Inner Body)

Figure 4:
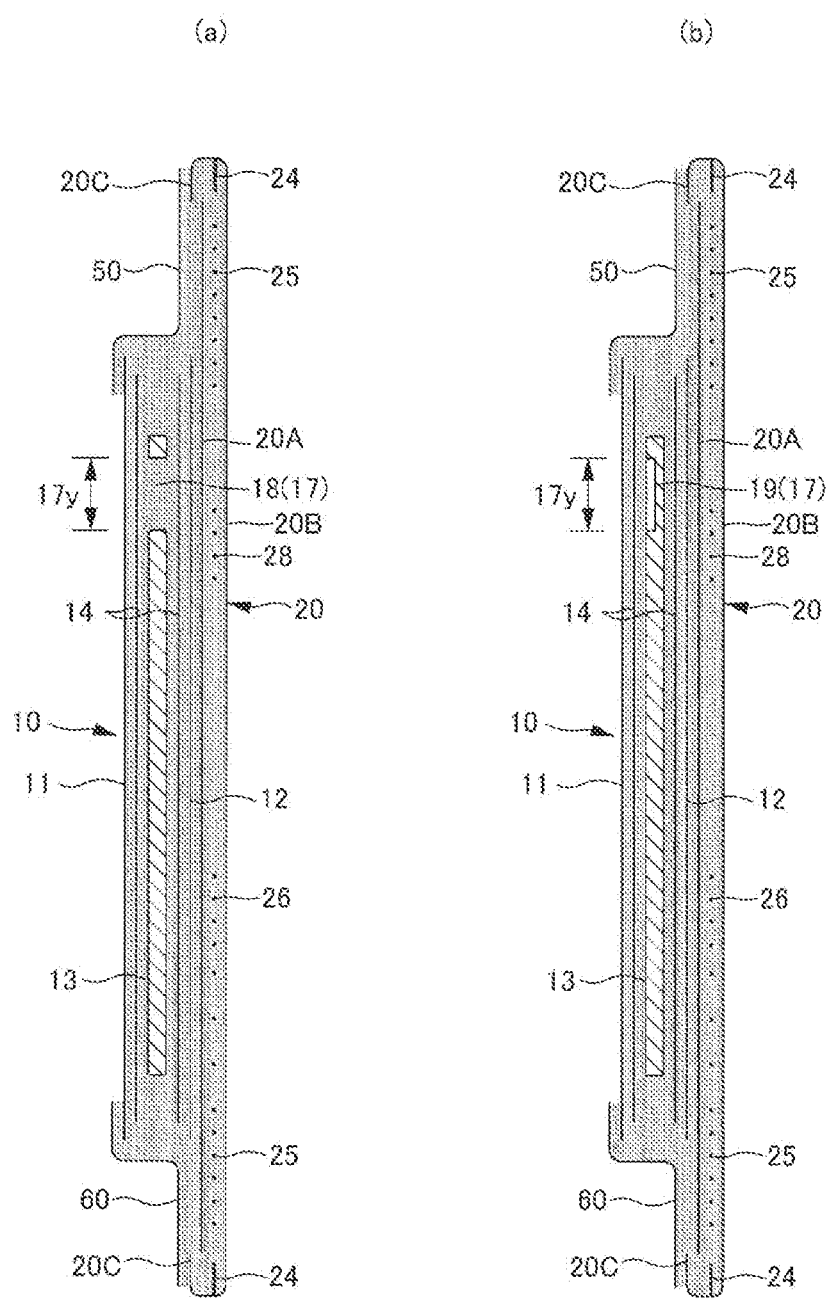
FIGS. 4(a) and 4(b) are cross-sectional views of FIG. 1 taken along line C-C.
Figure 5:
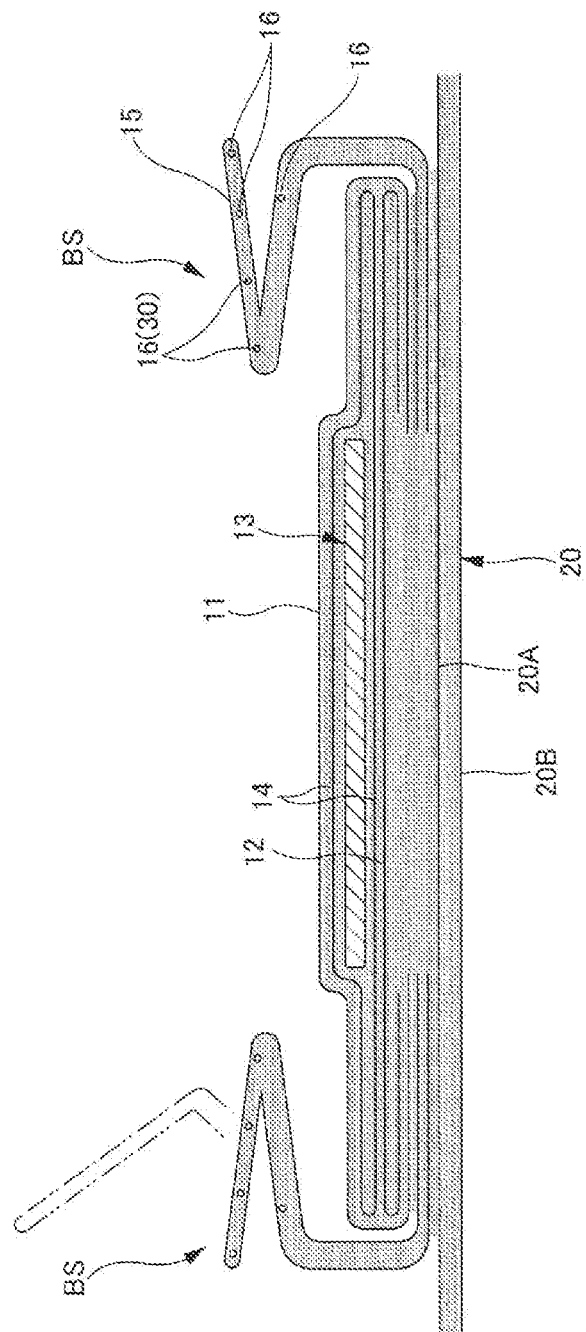
FIG. 5 is a cross-sectional view of FIG. 1 taken along line A-A.
Figure 6:
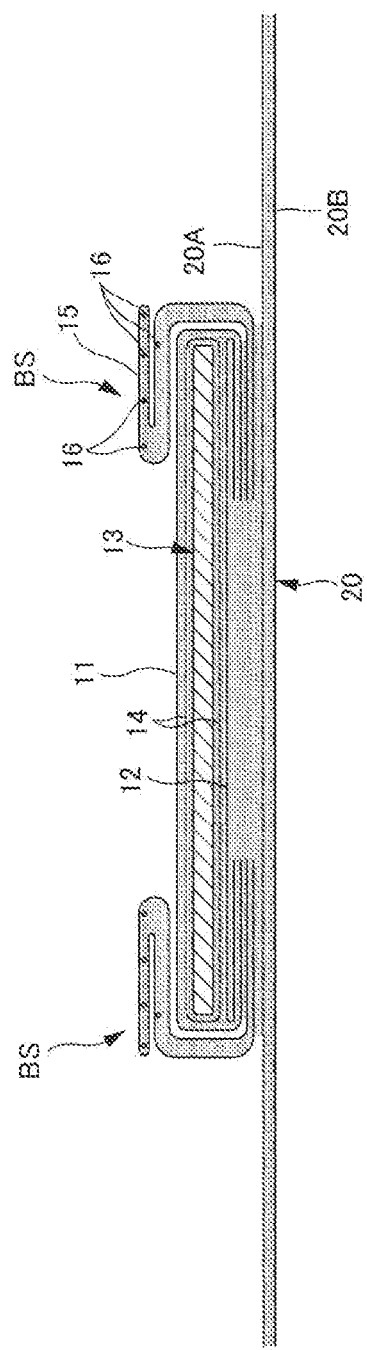
FIG. 6 is a cross-sectional view of FIG. 1 taken along line B-B.

As illustrated in FIGS. 4 to 6, the inner body 10 is structured such that the absorber 13 is interposed between the liquid pervious face sheet 11 made of non-woven fabric or the like and the liquid impervious back sheet 12 made of polyethylene or the like. The inner body 10 is intended to absorb and hold excretion having passed through the face sheet 11. Although there is no particular limitation on the planar shape of the inner body 10, the inner body 10 is generally shaped in an approximate rectangle as in the illustrated drawing.

The liquid pervious face sheet 11 covering the external side (skin-contacting side) of the absorber 13 is preferably a porous or non-porous non-woven fabric sheet or a porous plastic sheet. The raw fibers for non-woven fabric may be synthetic fibers based on olefin such as polyethylene or polypropylene, or synthetic fibers based on polyester or polyamide, or reproduced fibers of rayon or cupra, natural fibers of cotton or the like. The non-woven fabric may be produced by any appropriate processing method such as spun-lacing, spun-bonding, thermal bonding, melt-blowing, or needle punching. Among these processing methods, the spun-lacing method is excellent for flexibility and drape properties, and the thermal bonding method is excellent for bulkiness and softness. Forming a large number of through holes in the liquid pervious face sheet 11 would allow quick absorption of urine and the like and produce an excellent feeling of dryness. The liquid pervious face sheet 11 wraps around the side edges of the absorber 13 and extends up to the back surface of the absorber 13.

The liquid impervious back sheet 12 covering the back side (non-skin-contacting side) of the absorber 13 is made of a liquid impervious plastic sheet of polyethylene, polypropylene, or the like. However, in recent years, the liquid impervious plastic sheets with moisture perviousness have been used preferably from the viewpoint of prevention of stuffiness. The liquid impervious and moisture pervious sheet is a microporous sheet that is obtained by melting and kneading an inorganic filling agent in an olefin resin such as polyethylene, polypropylene, or the like to form a sheet and then elongating the sheet in a uniaxial or biaxial direction, for example.

The absorber 13 is basically made from a publicly known material, for example, accumulated pulp fibers, a filament assembly of cellulose acetate or the like, or non-woven fabric. The absorber 13 may include as necessary high-absorbent polymer particles mixed and fixed thereto. The absorber 13 can be wrapped as necessary with a package sheet 14 with liquid perviousness and liquid retention such as crepe paper for retention of the shape and the polymer.

The absorber 13 is shaped as a whole like a sand glass with a narrower part 13N smaller in width than the front and back sides of the crotch portion. However, the absorber 13 may have an arbitrary shape such as a rectangle. The dimensions of the narrower part 13N can be decided as appropriate. However, the length in the front-back direction of the narrower part 13N can be about 20 to 50% of the entire length of the diaper. The smallest width of the narrower part 13N can be about 40 to 60% of the entire width of the absorber 13. When the planar shape of the inner body 10 is an approximate rectangle with the narrower part 13N as described above, in the inner body 10, remaining parts without the absorber 13 are formed according to the narrower part 13N of the absorber 13.

The inner body 10 has three-dimensional gathers BS fitting around the legs on the both sides. As illustrated in FIGS. 5 and 6, each of the three-dimensional gathers BS is formed with a three-dimensional gather sheet 15 as a two-folded duplicate sheet including a fixation portion fixed to the side of the back surface of the inner body, a main unit portion extending from the fixation portion through the lateral side of the inner body to the side part of the front surface of the inner body, lying down portions formed by fixing the front end and back end of the main unit portion in a lying down state to the side parts of the front surface of the inner body, and a free portion formed in an un-fixed state between the lying down portions. Water-repellent non-woven fabric is preferably used for the three-dimensional gather sheet 15.

Elongated three-dimensional gather elastic members 16 are arranged at forward ends of the free portion in the duplicate sheet. The three-dimensional gather elastic members 16 are intended to stand the free portions protruding from the side edges of the absorber by their elastic stretching force as illustrated by the two-dot chain line in FIG. 5 to form the three-dimensional gathers BS in the product state.

The liquid impervious back sheet 12 is folded back together with the liquid pervious face sheet 11 on the width-direction both sides of the absorber 13. The liquid impervious back sheet 12 is desirably opaque so as not to allow the dark color of stool and urine to be seen through. To make the liquid impervious back sheet 12 opaque, plastic is preferably formed into a film with internal addition of a mixture of pigments and fillers such as calcium carbonate, titanium oxide, zinc oxide, white carbon, clay, talc, and barium sulfate.

The gather elastic members 16 can be made from a generally used material such as styrene-based rubber, olefin-based rubber, urethane-based rubber, ester-based rubber, polyurethane, polyethylene, polystyrene, styrene-butadiene, silicon, or polyester. To make the gather elastic members 16 hard to see from the outside, it is preferable that the gather elastic members 16 have a thickness of 925 dtex or less and are arranged under a tension of 150 to 350% at intervals of 10.0 mm or less. The gather elastic members 16 may be a thread type as illustrated in the drawing or a tape type with a certain width.

As the liquid pervious face sheet 11, the raw fibers for the three-dimensional gather sheets 15 may be synthetic fibers based on olefin such as polyethylene or polypropylene, polyester, polyamide, or reproduced fibers of rayon or cupra, natural fibers of cotton or the like. The non-woven fabric may be produced by any appropriate processing method such as spun-bonding, thermal bonding, melt-blowing, or needle punching. However, in particular, the non-woven fabric with low basis weight and high air permeability is preferably used for the three-dimensional gather sheets 15 for prevention of stuffiness. Further, the three-dimensional gather sheets 15 are desirably made from water-repellent non-woven fabric coated with a silicon-based, paraffin metal-based, or alkyl electrochromic chloride-based water repellent agent to prevent passage of urine or the like and rash on the wearer's body, and enhance the feel and texture (feeling of dryness).

(Structure Example of the Outer Body)

Figure 7:
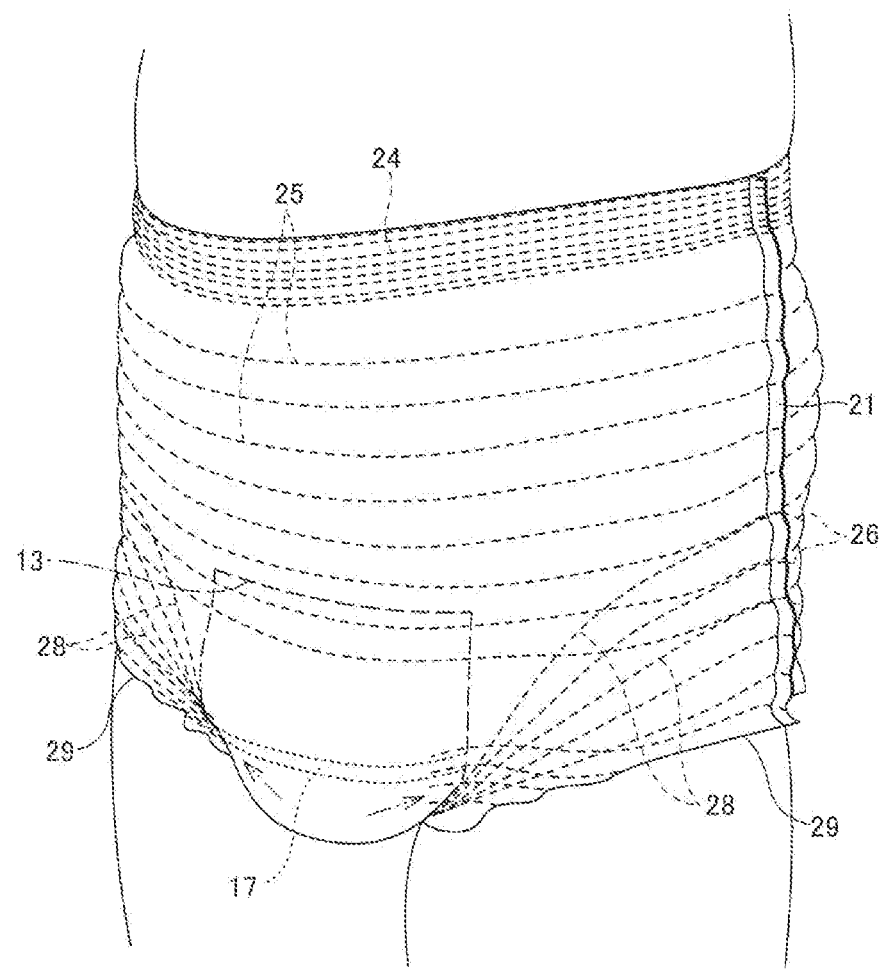
FIG. 7 is a perspective view of the underpants-type disposable diaper in a worn state.

The outer body 20 has a part constituting the front body F extending from the center in the front-back direction to the ventral side and a part constituting the back body B extending from the center in the front-back direction to the dorsal side. The front body F and the back body B are joined on the both sides to form the side seal portions 21 and form the waist opening through which the trunk of the wearer is passed and the pair of right and left leg openings through which the wearer's legs are passed as illustrated in FIG. 7.

The outer body 20 has a waist part T defined as a vertical range with the side seal portions 21 (from the waist opening to the upper ends of the leg openings) and a leg opening part L defined as a range in the front-back direction forming the leg openings (between the vertical area with the side seal portions 21 of the front body F and the vertical area with the side seal portions 21 of the back body B). The waist part T can be conceptually divided into a waist portion W forming the edge of the waist opening and a waist lower portion U as a portion below the waist portion W. In general, when the waist part T has boarders where the width-direction expansion and contraction stress changes (for example, the fineness or extension ratio of the resilient and elastic members changes), a side portion closer to the waist opening than to the boarder closest to the waist opening constitutes the waist portion W. When the waist part T does not have such boarders, a side portion closer to the waist opening than to the absorber 13 or to the inner body 10 constitutes the waist portion W.

The outer body 20 has a two-layer structure composed of a pressing sheet 20A and a back sheet 20B made of non-woven fabric or the like as illustrated in FIGS. 4 to 6. Various elastic members are arranged between the pressing sheet 20A and the back sheet 20B and between the non-woven fabrics of folded portions 20C formed by folding the waist opening edges of the back sheet 20B toward the inner surface side to impart elasticity. The planar shape of the outer body 20 is an approximate sand glass as a whole due to concave leg lines 29 formed on the both sides of the intermediate portion to make the leg openings.

The outer body 20 illustrated in the illustrated mode has, as width-direction elastic members in the front body F and the back body B, waist portion elastic members 24 arranged in the waist portion W, waist lower portion elastic members 25 arranged in the waist lower portion U, and leg opening elastic members 27 arranged in the leg opening part L. Besides, the outer body 20 includes curved elastic members 26 and 28 that curve and extend in a pattern from the side seal portions 21 toward the crotch portion along the leg openings. These elastic members 24 to 28 are fixed in the extended state at a predetermined extension ratio along their respective extending directions. The outer body 20 has no leg elastic members that continue from the side seal portions of the front body F to the side seal portions of the back body B around the leg lines 29.

The waist portion elastic members 24 are intended to elastically tighten the wearer's waist. The waist portion elastic members 24 are a plurality of elongated elastic members such as rubber threads attached in the extended state along the width direction between the layers in the waist portion W and provided at vertical intervals in the illustrated example. The waist portion elastic members 24 in the illustrated example are rubber threads but may be tape-like resilient and elastic members. The waist portion elastic members 24 in the illustrated example are sandwiched in the non-woven fabrics of the folded portions 20C of the back sheet 20B at the waist portion. Alternatively, the waist portion elastic members 24 may be sandwiched between the pressing sheet 20A and the back sheet 20B. The waist portion elastic members 24 are desirably provided in the entire waist portion W in the width direction.

The waist lower portion elastic members 25 are intended to fit the diaper elastically to the wearer's lower abdominal region and gluteal region. In the illustrated example, the waist lower portion elastic members 25 are a plurality of elongated elastic members such as rubber threads arranged in the extended state along the width direction between the layers in the waist lower portion U and provided at vertical intervals. The waist lower portion elastic members 25 are provided in the waist lower portion U at least on the width-direction both sides of the width-direction intermediate portion of the absorber, and the side edges of the waist lower potion elastic members 25 are desirably provided up to the side seal portions 21.

The leg opening elastic members 27 are intended to impart width-direction elasticity to the portions along the leg openings. In the illustrated example, the leg opening elastic members 27 are a plurality of elongated elastic members arranged in the extended state along the width direction between the layers in the leg opening part L and provided at vertical intervals. The leg opening elastic members 27 are provided in the leg opening part L at least on the width-direction both sides of the width-direction intermediate portion of the absorber, and the side edges of the leg opening elastic members 27 are desirably provided up to the leg opening edges 29.

Besides the waist portion elastic members 24, the waist lower portion elastic members 25, and the leg opening elastic members 27, the curved elastic members 26 and 28 composed of elongated elastic members such as rubber threads are arranged along predetermined curve lines in the range of the outer body 20 across from the waist part T to the leg opening part L. The number of the curved elastic members 26 may be one but is preferably plural. In the illustrated example, the curved elastic members 26 are four elongated elastic members such as rubber threads. The curved elastic members 26 and 28 are arranged at intervals without crossing with each other. For the curved elastic members 26 and 28, about two or three elastic members may be arranged as a substantial bundle at small intervals therebetween, or three or more, preferably four or more elastic members may be arranged at intervals of about 3 to 20 mm, preferably about 6 to 16 mm, to form a predetermined stretchable zone.

Figure 8:
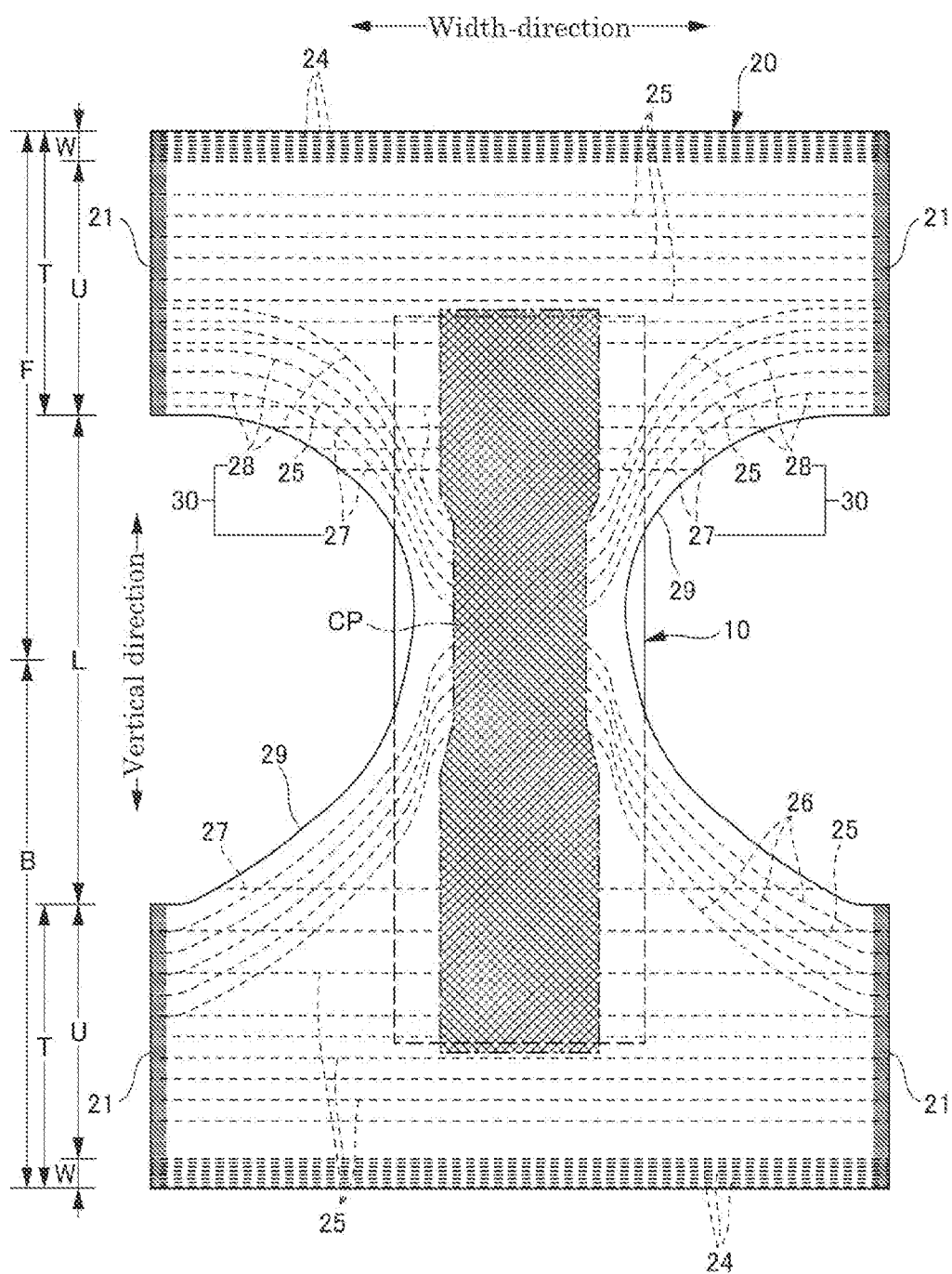
FIG. 8 is a plane view of major components of the underpants-type disposable diaper.
Figure 9:
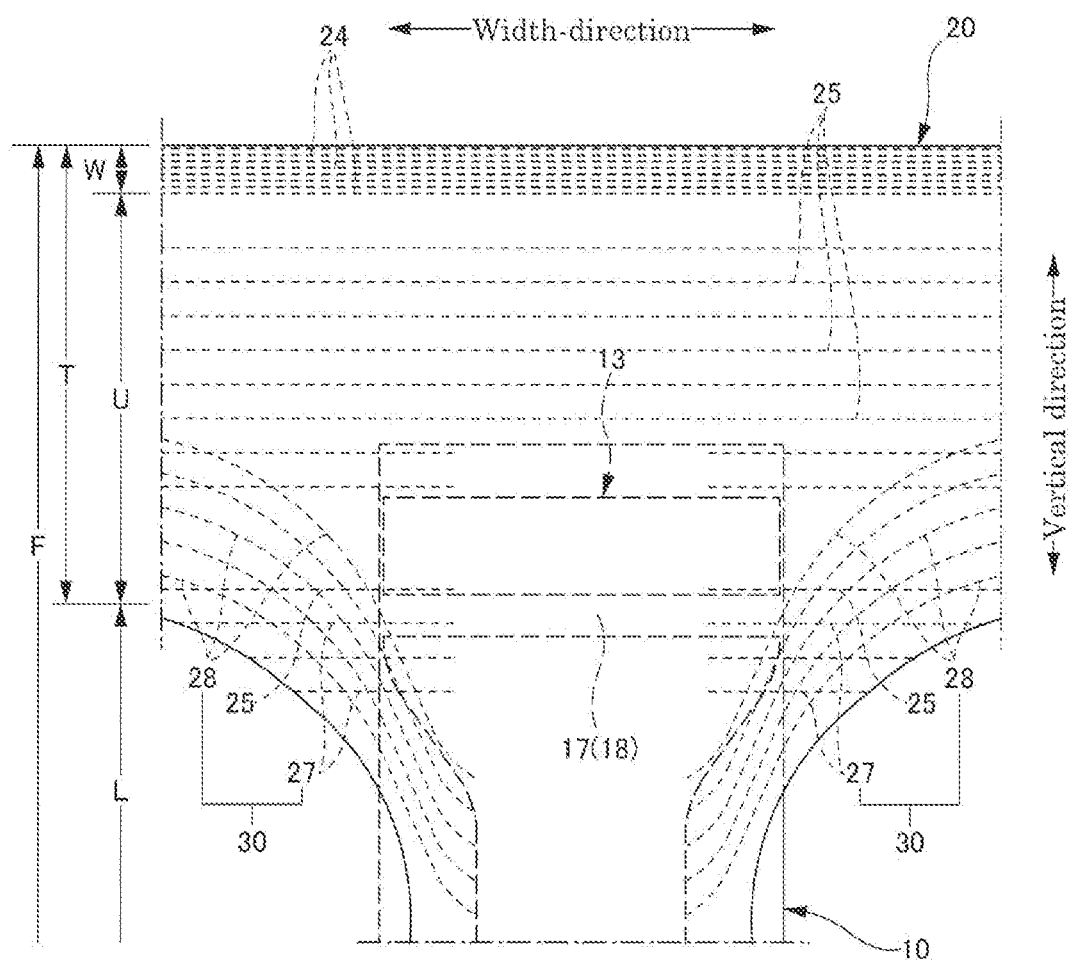
FIG. 9 is an enlarged plane view (outer surface side) of major components of the underpants-type disposable diaper.

As illustrated in FIG. 8, in manufacturing, the waist lower portion elastic members 25, the leg opening elastic members 27, and the curved elastic members 26 and 28 are arranged and continuously fixed to the outer body 20, and then, some or all of the elastic members overlapping the absorber 13 may be finely cut in a predetermined cutting pattern CP to form a non-contraction part on which no contraction force acts (that is, the part overlapping the cutting pattern CP in FIG. 8), and to form parts extending laterally from the non-contraction part as contraction parts on which contraction force acts (that is, the parts where the waist lower portion elastic members 25 and the curved elastic members 26 and 28 are left in the continuous state on closer to lateral sides than to the cutting pattern CP in FIG. 8). Accordingly, when being continuously provided from one side seal portion 21 to the other (opposite) side seal portion 21 crossing over the absorber 13, some or all of the waist lower portion elastic members 25, the leg opening elastic members 27, and the curved elastic members 26 and 28 overlapping the absorber 13 are finely cut. This prevents too large width-direction contraction of the absorber 13. As a matter of course, the waist lower portion elastic members 25, the leg opening elastic members 27, and the curved elastic members 26 and 28 may be arranged continuously crossing over the absorber 13. As being understood from the foregoing description, "providing the elastic members" in the present invention means providing the contraction part on which the contraction force of the elastic members acts, and this is not applied to the non-contraction parts where the contraction force of the elastic members is suppressed by cutting the elastic members.

The outer body 20 can be manufactured by the technique described in JP-A No. 4-28363 or JP-A No. 11-332913, for example. In addition, the curved elastic members 26 and 28 can be preferably cut and made discontinuous on the inner body 10 by employing the cutting technique described in JP-A No. 2002-35029, JP-A No. 2002-178428, or JP-A No. 2002-273808.

Unlike in the illustrated example, the curved elastic members 26 and 28 may be provided only in either of the front body F and the back body B. When the curved elastic members 26 and 28 are provided in both the front body F and the back body B, some or all of the group of curved elastic members 28 arranged in the front body F and some or all of the group of curved elastic members 26 arranged in the back body B may cross each other (not illustrated). However, in a preferred mode, the group of curved elastic members 28 arranged in the front body F and the group of curved elastic members 26 arranged in the back body B do not cross each other, but separate from each other in the vertical direction at the intermediate portion in the front-back direction, in particular, at the position slightly closer to the front body F.

Further, the curved elastic members 26 and 28 may not be curved entirely but may have linear parts.

The extension ratios of the elastic members 24 to 28 in attaching can be decided as appropriate. However, for a general diaper for adults, the extension ratio of the waist portion elastic members 24 can be about 160 to 320%, the extension ratio of the waist lower portion elastic members 25 and the leg opening elastic members 27 can be about 160 to 320%, and the extension ratio of the curved elastic members 26 and 28 can be about 230 to 320%.

(Front and Back Pressing Sheets)

As also illustrated in FIGS. 1 and 4, front and back pressing sheets 50 and 60 may be provided to cover the front and back end portions of the inner body 10 on the inner surface of the outer body 20 and prevent leakage from the front and back edges of the inner body 10. The illustrated mode will be described more in detail. The front pressing sheet 50 extends on the inner surface of the front body F in the width direction entirely from the inner surface of the folded portion 20C at the waist-side end to the part overlapping the front end part of the inner body 10. The back pressing sheet 60 extends on the inner surface of the back body B in the width direction entirely from the inner surface of the folded portion 20C at the waist-side end to the part overlapping the back end part of the inner body 10. The front and back pressing sheets 50 and 60 can have small non-bonded portions at the entire crotch lower side edges in the width direction (or only at the central portion) to prevent the adhesive from squeezing out and allow the non-bonded portions to lift slightly from the face sheet and serve as leak prevention walls.

Attaching the front and back pressing sheets 50 and 60 as separate members as in the illustrated mode would provide the advantage of a higher degree of freedom of material selection but also provide the disadvantage of increase in the numbers of materials and manufacturing processes. Accordingly, the folded portions 20C formed by folding the outer body 20 toward the inside of the diaper may be extended up to the parts overlapping the inner body 10 to form the parts equivalent to the pressing sheets 50 and 60.

(Vertical Stretchable Part)

Figure 10:
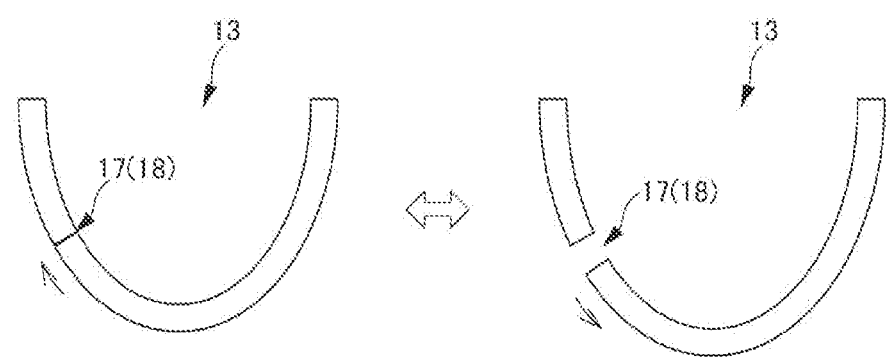
FIG. 10 is a cross-sectional view conceptually illustrating extension and contraction of the absorber.

Characteristically, as illustrated in FIGS. 1 to 4 and 9, a vertical stretchable part 17 vertically extending and contracting in length is provided in the vertical intermediate portion of the absorber 13 in the front body F, and lifting elastic members 30 having contraction force of lifting the portion of the vertical stretchable part 17 on the side more backward than the front end portion to the width-direction both sides and obliquely upward side (see the two-dot chain arrows in FIG. 7) when the diaper is worn are provided on closer to lateral sides than to the width-direction intermediate portion of the absorber 13 in the outer body 20 of the front body F. The vertical stretchable part 17 is vertically extended and contracted in length by the elastic extension and contraction of the lifting elastic members 30 as illustrated in FIG. 10. Therefore, the vertical stretchable part 17 is vertically extended and contracted in length to maintain the fit by the elastic extension and contraction of the lifting elastic members 30 in accordance with dynamic changes such as the wearer's motion and changes in the volume of the absorber 13 between before and after absorption, thereby providing a more excellent dynamic fit. In addition, the lifting elastic members 30 are provided on closer to the lateral sides than to the width-direction intermediate portion of the absorber 13 as are conventionally done, and the absorber 13 does not contract largely.

The vertical stretchable part 17 may be an accordion-like folded part or a part lowered in rigidity than the neighboring parts by mechanical processing such as embossing as far as it is a part where the absorber 13 is vertically extended and contracted in length. However, from the viewpoint of ease of manufacture, the vertical stretchable part 17 is desirably a slit 18 that is continuous on the entire absorber 13 in the width direction as illustrated in FIGS. 3(a) and 4(a), or a low-basis weight part 19 that is continuous on the entire absorber 13 in the width direction as illustrated in FIGS. 3(b) and 4(b).

A vertical dimension 17y of the vertical stretchable part 17 can be decided as appropriate. However, when the vertical dimension 17y is too small, the amount of stretch will decrease, and when the vertical dimension 17y is too large, this may exert a harmful effect on absorption performance. Accordingly, the vertical dimension 17y is preferably about 3 to 8 mm, in particular about 3 to 5 mm.

Figure 11:
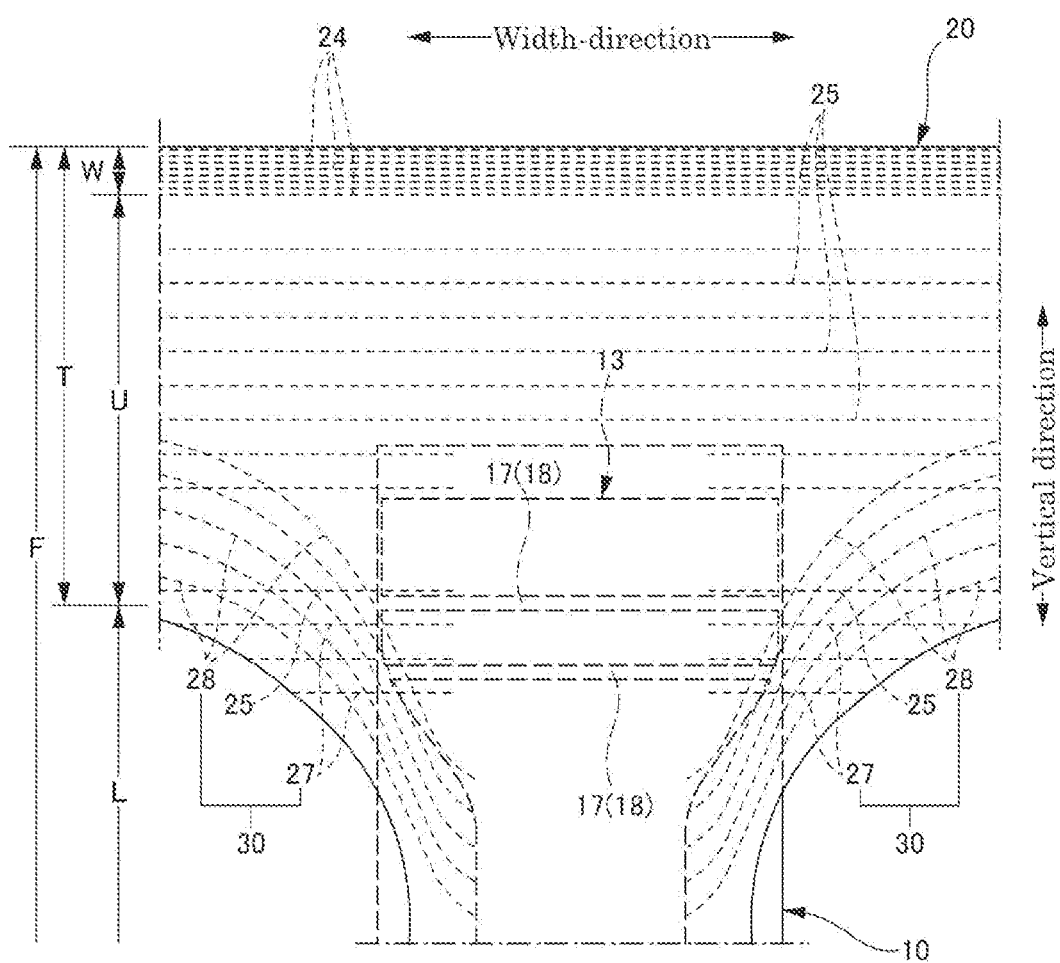
FIG. 11 is an enlarged plane view (outer surface side) of major components of the underpants-type disposable diaper.

The vertical stretchable part 17 may be provided in one place as illustrated in FIGS. 1 to 3(a) or in plural places at vertical intervals as illustrated in FIG. 11. In the case of forming the vertical stretchable part 17 as the slit 18 or the low-basis weight part 19, when the vertical stretchable part 17 is longer in the front-back direction, the vertical stretchable part 17 will decrease in diffusivity in the front-back direction. On the other hand, when a plurality of vertical stretchable parts 17 is provided at vertical intervals, the dimension in the front-back direction of one vertical stretchable part 17 will become shorter even though the total stretching length of the vertical stretchable parts 17 is the same as the length of the long vertical stretchable part. This makes it possible to suppress reduction in the diffusivity in the front-back direction.

The position in the front-back direction of the vertical stretchable part 17 can be decided as appropriate. However, in general, assuming that the front end of the underpants-type disposable diaper (the edge of the waist opening of the front body F) is in a position of 0% and the back end of the underpants-type disposable diaper (the edge of the waist opening of the back body B) is in a position of 100%, the vertical stretchable part 17 is preferably arranged in a position of 10 to 47%, in particular, in a position of 12 to 45%.

The shape of the vertical stretchable part 17 can be decided as appropriate. However, when the vertical stretchable part 17 is shaped such that a front edge 17f is curved backward, a back edge 17b is curved forward, or both as illustrated in FIG. 3(c), the part of the absorber 13 on the front side of the vertical stretchable part 17 is likely to swing from side to side with respect to the part on the back side of the vertical stretchable part 17, thereby providing a more excellent dynamic fit.

There is no particular limitation on the lifting elastic members 30 as far as they are provided on closer to lateral sides than to the width-direction intermediate portion of the absorber 13 in the outer body 20 of the front body F and have contraction force of lifting the portion of the vertical stretchable part 17 on the back side of the front end portion to the width-direction both sides and the obliquely upward side at least when the diaper is worn. In the illustrated mode, the leg opening elastic members 27 and the curved elastic members 26 and 28 lift the portion of the vertical stretchable part 17 on the rear side of the front end portion to the width-direction both sides and the obliquely upward side at least when the diaper is worn, thereby to constitute the lifting elastic members 30. The leg opening elastic members 27 extend along the width direction when the diaper is opened. However, as can be understood from the worn state illustrated in FIG. 7, when the diaper is worn, the leg opening elastic members 27 are oriented obliquely upward in the lateral direction because the width-direction both sides of the diaper are lifted relatively upward, and thus the leg opening elastic members 27 exert contraction force in that direction. Accordingly, some of the leg opening elastic members 27 positioned in the portion of the vertical stretchable part 17 on the back side of the front end portion constitute the lifting elastic members 30.

Meanwhile, the curved elastic members 26 and 28 are oriented obliquely upward in the lateral direction and exert contraction force in that direction when the diaper is opened and also when the diaper is worn. Accordingly, some of the curved elastic members 26 and 28 with absorber 13-side end portions positioned on the back side of the front end portion of the vertical stretchable part 17 constitute the lifting elastic members 30. When the existing elastic members do not constitute the lifting elastic members 30 unlike in this example or when the existing elastic members constitute the lifting elastic members 30 but the lifting action needs to be further enhanced, lifting elastic members 30 may be additionally provided.

Extending the lifting elastic members 30 up to the positions overlapping the side parts of the absorber 13 would provide more excellent lifting effect. However, the lifting elastic members 30 may coincide with the side edges of the absorber 13 or separate laterally from the side edges of the absorber 13.

The contraction force of the lifting elastic members 30 may be equal to the contraction force of the other elastic members (the waist lower portion elastic members 25 in the illustrated mode (equivalent to the basic elastic members). However, the contraction force of the lifting elastic members 30 is preferably decreased to make a difference so that the outer body 20 can be fitted firmly by the waist lower portion elastic members 25 and the leg opening elastic members 27 and the vertical stretchable part 17 can easily move with the firmed fit as a support. The contraction force takes on values at the same extension ratio and can be made different by a publicly known method depending on the kind of the elastic members, the extension ratio of the elastic members in attaching, the fineness of the elastic members, or the like.

Figure 12:
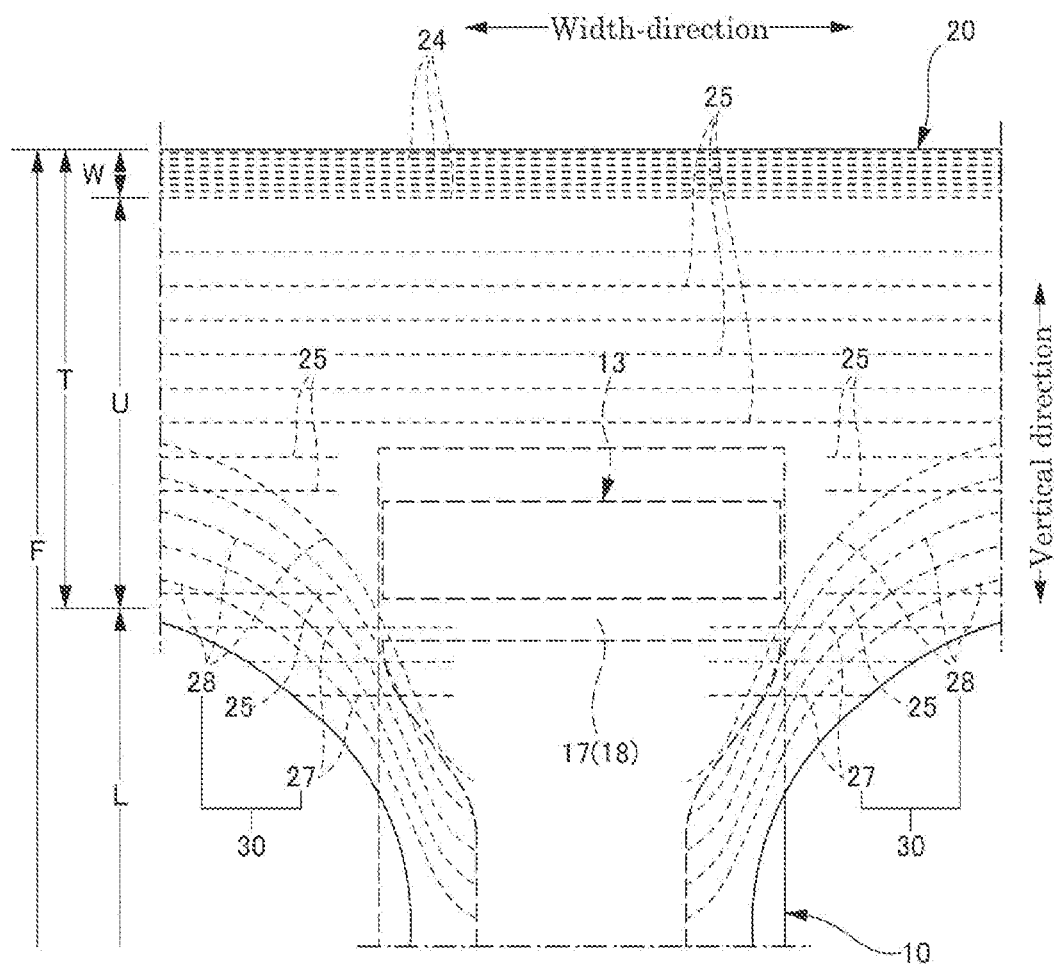
FIG. 12 is an enlarged plane view (outer surface side) of major components of the underpants-type disposable diaper.

In the modes illustrated in FIGS. 1 to 8, the waist lower portion elastic members 25 (equivalent to the side portion elastic members) that are positioned on closer to lateral sides than to the width-direction intermediate portion of the absorber but do not constitute the lifting elastic members 30 have end portions positioned on the width-direction central side that overlap in the width direction the side parts of the absorber 13 in the same manner as the end portions of the lifting elastic members 30 on the width-direction central side. In that case, the lifting action of the lifting elastic members 30 is likely to be affected by the contraction force of the waist lower portion elastic members 25. Accordingly, in a preferred mode as illustrated in FIG. 12, the end portions of the waist lower portion elastic members 25 positioned on the width-direction central side but not constituting the lifting elastic members 30 are laterally more separated from the side edges of the absorber 13 than the end portions of the lifting elastic members 30 on the width-direction central side. Accordingly, it is possible to ensure the basic fit of the absorber 13 on the width-direction both sides so that the lifting action of the lifting elastic members 30 becomes less affected by the contraction force of the other elastic members and acts more directly on the vertical stretchable part 17.

(Others)

In the foregoing example, the integral outer body 12 covers continuously from the front body F to the back body B. In an alternative mode, the outer body may be divided into the part constituting the front body F and the part constituting the back body B such that the outer body of the front body F and the outer body of the back body B are not continuous at the crotch portion but separated from each other (not illustrated). In this case, the outer body of the front body has a portion overlapping at least the vertical stretchable part, sections on the width-direction both sides of the portion, and an area on the waist opening side of the portion and the sections. In addition, the back surface of the inner body can be covered with the crotch portion outer body of non-woven fabric or the like.

INDUSTRIAL APPLICABILITY

The present invention is applicable to the underpants-type disposable diapers as in the example described above.

REFERENCE SIGNS LIST

B Back body
BS Three-dimensional gather
F Front body

10 Inner body
11 Face sheet
12 Liquid impervious back sheet
13 Absorber
13N Narrower part
14 Package sheet
15 Three-dimensional gather sheet
16 Three-dimensional gather elastic member
17 Vertical stretchable part
20 Outer body
20C Folded portion
21 Side seal portion
24 Waist portion elastic member
25 Waist lower portion elastic member
26 and 28 Curved elastic member
29 Leg line
30 Lifting elastic member
27 Leg opening elastic member
T Waist part
L Leg opening part
W Waist portion
U Waist lower portion
18 Slit
19 Low-basis weight part

The invention claimed is:

1. An underpants-type disposable diaper comprising:
an outer body forming individually or integrally a front body and a back body; and
an absorber provided on the inner side of the outer body ranging from the front body to the back body,
the outer body of the front body and the outer body of the back body being joined together at both side edges to form side seal portions, thereby forming a waist opening and a pair of right and left leg openings, wherein
a vertical stretchable part is provided in a vertical intermediate portion and a same layer of the absorber in the front body,
the outer body of the front body has a portion overlapping at least the vertical stretchable part,
lifting elastic members are provided in the outer body of the front body closer to lateral sides than to a width-direction intermediate portion of the absorber, wherein, when the diaper is worn, the lifting elastic members are configured to provide a contraction force of lifting a portion of the vertical stretchable part upward, and
the vertical stretchable part vertically extends and contracts in length by elastic extension and contraction of the lifting elastic members.

2. The underpants-type disposable diaper according to claim 1, wherein
leg opening elastic members composed of elongated elastic members along a width direction are provided in the outer body of the front body in vertical ranges corresponding to the leg openings on closer to lateral sides than to the width-direction intermediate portion of the absorber, and
when the diaper is worn, the leg opening elastic members are oriented obliquely upward in a lateral direction and at least some of the leg opening elastic members constitute the lifting elastic members.

3. The underpants-type disposable diaper according to claim 1, wherein
the outer body of the front body includes basic elastic members, which are different from the lifting elastic members, below a waist portion to improve a fit, and
the contraction force of the lifting elastic members is smaller than a contraction force of the basic elastic members at a same elongation percentage.

4. The underpants-type disposable diaper according to claim 1, wherein
the outer body of the front body includes side portion elastic members, which are different from the lifting elastic members, on closer to lateral sides than to the width-direction intermediate portion of the absorber to improve a fit, and
end portions of the side portion elastic members on a width-direction central side are laterally more separated from side edges of the absorber than end portions of the lifting elastic members on a width-direction central side.

5. The underpants-type disposable diaper according to claim 1, wherein the outer body of the front body includes curved elastic members composed of elongated elastic members arranged from the side seal portions to a crotch portion along the leg openings, and at least some of the curved elastic members constitute the lifting elastic members.

6. The underpants-type disposable diaper according to claim 1, wherein the vertical stretchable part is a slit or a low-basis weight part continuous on the entire absorber in the width direction, and wherein at least two of the vertical stretchable parts are provided at vertical intervals.

7. The underpants-type disposable diaper according to claim 1, wherein the vertical stretchable part has a front edge curved backward or a back edge curved forward, or both.

* * * * *